US010245000B2

(12) United States Patent
Bar-Shalev et al.

(10) Patent No.: US 10,245,000 B2
(45) Date of Patent: Apr. 2, 2019

(54) METHOD AND SYSTEM FOR DEFINING A VOLUME OF INTEREST IN A PHYSIOLOGICAL IMAGE

(71) Applicant: General Electric Company, Schenectady, NY (US)

(72) Inventors: Avi Bar-Shalev, Tirat Carmel (IL); Jonathan Sachs, Tirat Carmel (IL); Yaron Hefetz, Kibbutz Alonim (IL)

(73) Assignee: General Electric Company, Schenectady, NY (US)

( * ) Notice: Subject to any disclaimer, the term of this patent is extended or adjusted under 35 U.S.C. 154(b) by 1130 days.

(21) Appl. No.: 14/568,245

(22) Filed: Dec. 12, 2014

(65) Prior Publication Data
US 2016/0166220 A1 Jun. 16, 2016

(51) Int. Cl.
| *A61B 6/00* | (2006.01) |
| *A61B 6/03* | (2006.01) |
| *A61B 5/055* | (2006.01) |
| *A61B 5/107* | (2006.01) |
| *A61B 5/00* | (2006.01) |

(Continued)

(52) U.S. Cl.
CPC .......... *A61B 6/5205* (2013.01); *A61B 5/0035* (2013.01); *A61B 5/055* (2013.01); *A61B 5/1076* (2013.01); *A61B 6/032* (2013.01); *A61B 6/037* (2013.01); *A61B 6/4417* (2013.01); *A61B 6/5229* (2013.01); *A61B 6/5235* (2013.01); *A61B 6/5258* (2013.01); *G06T 7/11* (2017.01); *G06T 7/174* (2017.01); *G06T 2207/10081* (2013.01); *G06T 2207/10104* (2013.01); *G06T 2207/10108* (2013.01)

(58) Field of Classification Search
CPC ... A61B 6/5205; A61B 6/5258; A61B 6/5229; A61B 5/1076; A61B 5/0035; A61B 6/032; A61B 5/055; A61B 6/5235; A61B 6/037; A61B 6/4417; G06T 2207/10108; G06T 2207/10104; G06T 2207/10081; G06T 7/174; G06T 7/11
See application file for complete search history.

(56) References Cited

U.S. PATENT DOCUMENTS

| 7,529,335 B2 | 5/2009 | Bruder et al. |
| 8,068,578 B2 | 11/2011 | Krauss |
| 8,121,374 B2 | 2/2012 | Schechter |

(Continued)

OTHER PUBLICATIONS

Marta et al. Partial Volume Effect Correction using Segmented CT Images with Distance Mapping. Sixth Hungarian Conference on Computer Graphics and Geometry, Budapest, 2012.*

*Primary Examiner* — Amelie R Gillman
(74) *Attorney, Agent, or Firm* — Dean D. Small; The Small Patent Law Group, LLC

(57) ABSTRACT

A method and apparatus for defining a volume of interest in a physiological image based upon an anatomical image. The method and system acquires an anatomical image of a volume of interest using a first imaging modality. A physiological image is acquired using a second imaging modality different from the first imaging modality. An outline of the volume of interest is defined on the anatomical image and applied to the physiological image to define the volume of interest m the physiological image. Based upon the outline, the system and method assigns binary values to voxels within the outline to more accurately define the volume of interest.

7 Claims, 9 Drawing Sheets

(51) Int. Cl.
 *G06T 7/11* (2017.01)
 *G06T 7/174* (2017.01)

(56) References Cited

U.S. PATENT DOCUMENTS

| | | |
|---|---|---|
| 8,284,892 B2 | 10/2012 | Pack et al. |
| 8,391,578 B2 | 3/2013 | Bar-Shalev |
| 8,421,021 B2 | 4/2013 | Sachs et al. |
| 8,712,124 B2 | 4/2014 | Sachs et al. |

* cited by examiner

METHOD AND SYSTEM FOR DEFINING A VOLUME OF INTEREST IN A PHYSIOLOGICAL IMAGE

BACKGROUND OF THE INVENTION

The subject matter disclosed herein relates generally to a multi-modality medical imaging system. More particularly, the present disclosure relates to a system and method for defining a volume of interest on an image from a first imaging modality system based on information acquired from an image from a second imaging modality system and calculating relevant, medical parameters from the defined volume.

Single Photon Emission Computed Tomography (SPECT) imaging systems and Positron Emission Tomography (PET), referred to jointly as nuclear or NM imaging systems, generally acquire images showing physiological data based on the detection of radiation from the emission of photons. Images acquired using SPECT and/or PET are referred to as physiological images and may be used to evaluate different conditions and diseases that affect the heart or lungs, for example. Such conditions may include the size of a cancerous tumor or lesion.

SPECT and PET scans are increasingly being used in connection with other types of medical scans, including, for example, with Computed Tomography (CT) scans. CT scans generate anatomical images that are typically obtained at a much higher resolution as compared to the lower resolution physiological image from a SPECT or PET scan. The combination of the images from the scans from the two different imaging modalities, often referred to as co-registration, provides both anatomic and physiological information on a single image. Combination or multimodality imaging systems are also available to perform both scans during the same scanning session.

Since the physiological image from the SPECT or PET scan is taken at a low resolution and the image may be noisy, it is often difficult to define the outer boundaries of the organ or lesion being examined (referred to as the target); however these boundaries are generally clearly visible in the anatomical images. As a result, the physiological images acquired from the SPECT or PET system may not include accurate volumetric measurement of the organ or lesion being examined. Additionally, anatomical structures, such as neighboring chest bones and lungs, each having different densities, may cause significant variations in the volume of the region being reviewed when using only the physiological image.

Medically relevant parameters are derived from the physiological images from the NM imaging systems. These parameters can include the total radiopharmaceutical activity in the target, the average concentration of radiopharmaceutical activity in the target, and/or the ratio of average concentration of radiopharmaceutical activity in the target to the average concentration of radiopharmaceutical activity in the surrounding tissue (referred as "background"). Inaccuracies in defining, the boundaries of the target, and "smearing" of the physiological images due to the low resolution of NM imaging system causes inaccuracies in the calculated parameters.

SUMMARY OF THE INVENTION

The present disclosure generally relates to a multi-modality medical imaging system. More specifically, the present disclosure relates to a method and system for determining the radiopharmaceutical distribution within a target in a physiological image. The method includes acquiring a physiological image utilizing a first imaging modality, such as a nuclear (NM) imaging system. The method further requires acquiring an anatomical image utilizing a separate, distinct imaging modality, such as a CT or MRI imaging system. Once both the anatomical image and physiological image are obtained, the method identifies a target boundary of the target within an area of interest in the anatomical image. Since the anatomical image acquired from the second imaging modality is typically acquired at a much higher resolution, the identification of the target boundary in the area of interest in the anatomical image more accurately define the shape and volume of the target.

Once the target boundary for the target has been generated from the anatomical image, the system and method of the present disclosure applies the target boundary to the physiological image. Since the physiological image is typically obtained at a much lower resolution as compared to the anatomical image, the target boundary identified in the anatomical image will more accurately define the target within the area of interest.

Once the target boundary has been applied to the physiological image, radiopharmaceutical distribution in the physiological image can be enhanced. By utilizing the combined image in which the target boundary is defined utilizing the higher resolution and more accurate and accuracy anatomical image, the system and method of the present disclosure can create a more accurate determination of relevant medical parameters from the physiological image.

In one embodiment of the disclosure, the system and method utilizes an image enhancement module to enhance the physiological image. The image enhancement module includes a mask construction module that functions and operates to generate a target boundary of a target included in the anatomical image. Once the boundary of the target has been generated, a registration module overlays the boundary in proper registration with the physiological image. With the target boundary in place, the method and system of the present disclosure modifies an activity level in partial volume voxels in the physiological image.

In one embodiment of the disclosure, an inner activity value is calculated by summing the activity level of the voxels completely within the target boundary. The method identifies partial volume voxel that include the target boundary. For the partial volume voxels, a weight is assigned that is based on the amount of the voxel inside and outside of the target boundary. Based on the weight, the system and method calculates a partial volume activity value by summing the modified activity levels for the partial volume voxels. Additionally, a corrected physiological image may be constructed and displayed by adjusting the measured physiological image values based on the target boundary determined from the anatomical image and the assumption that the target and non-target physiological behaviors are distinct.

Various other features, objects and advantages of the invention will be made apparent from the following description taken together with the drawings.

BRIEF DESCRIPTION OF THE DRAWINGS

The drawings illustrate the best mode presently contemplated of carrying out the disclosure. In the drawings.

DETAILED DESCRIPTION OF THE INVENTION

Figure 1:
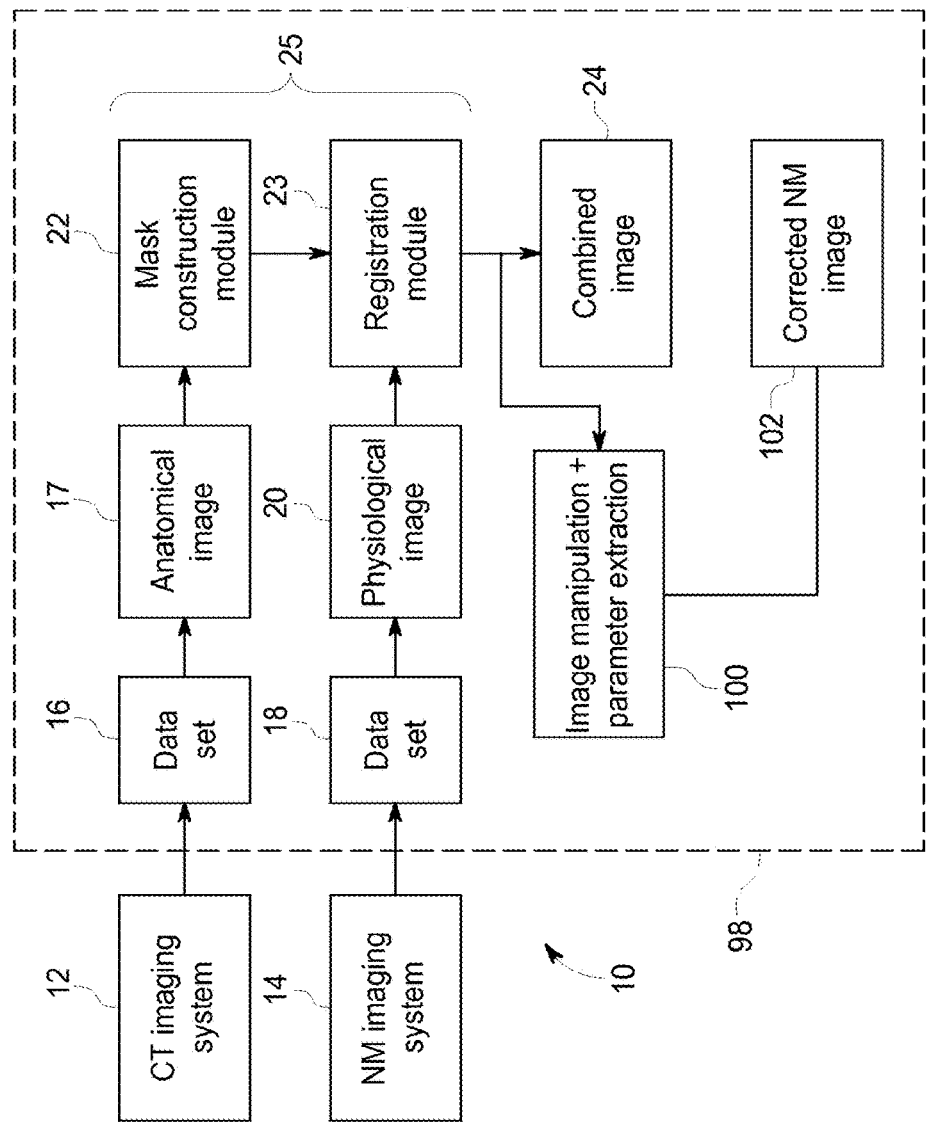
FIG. 1 is a schematic block diagram of an exemplary imaging system in accordance with various embodiments of the disclosure.

In the present description, certain terms have been used for brevity, clearness and understanding. No unnecessary limitations are to be applied therefrom beyond the requirement of the prior art because such terms are used for descriptive purposes only and are intended to be broadly construed. The different systems and methods described herein may be used alone or in combination with other systems and methods. Various equivalents, alternatives and modifications are possible within the scope of the appended claims. Each limitation in the appended claims is intended to invoke interpretation under 35 U.S.C. § 112, sixth paragraph, only if the terms "means for" or "step for" are explicitly recited in the respective limitation.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g. processors or memories) may be implemented in a single piece of hardware (e.g., a general purpose signal processor or a block of random access memory, hard disk, or multiple pieces of hardware). Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the phrase "image" is not intended to exclude embodiments of the present invention in which data representing an image is generated, but a viewable image is not. Therefore, as used herein the term "image" broadly refers to both viewable images and data representing a viewable image. However, many embodiments generate, or are configured to generate, at least one viewable image.

FIG. 1 is a schematic block diagram of an exemplary combined imaging system 10 operating and organized in accordance with an embodiment of the present invention. In the exemplary embodiment, the imaging system 10 is a multi-modality imaging system that includes two different imaging modality units; an anatomical imaging system 12 and physiological imaging system 14. The different imaging, modalities may include a Positron Emission Tomography (PET), a Single Photon Emission Computed Tomography (SPECT), a Computed Tomography (CT), an ultrasound system, a Magnetic Resonance Imaging (MRI) or any other system capable of generating tomographic images. In one exemplary embodiment, the first modality unit 12 is a CT imaging system or an MRI system and the second modality unit 14 is one of a PET imaging system or a SPECT imaging system, referred to herein as a nuclear or NM imaging system 14. It should be noted that the method according to various embodiments described herein may be used with a 3D anatomical image of a patient taken with a first single modality system such as a CT or MRI and a 3D physiological image of the same patient taken by a second single modality such as SPECT or PET.

During operation, the CT imaging system 12 is used to scan at least a section of a patient to acquire sinogram data, referred to herein as a transmission data set 16 of an organ of interest. The transmission data set 16 is then used to reconstruct an anatomical or structural image 17 of the volume of interest that includes the organ of interest. In the exemplary embodiment, the transmission data set 16 is processed to reconstruct a three-dimensional (3D) anatomical image 17 that corresponds to a plurality of two-dimensional (2D) slices taken through the organ of interest. In one embodiment, the 3D anatomical image may be reconstructed using a filtered back projection technique. Alternatively, other reconstruction methods may be used as known in the art. The filtered back projection technique converts the attenuation measurements from a scan into integers called "CT numbers" or "Hounsfield units", which are used to control the brightness of a corresponding pixel. The reconstructed slices are then combined to form the three-dimensional anatomical image of the organ of interest. The anatomical image 17 is a high resolution image having clear and defined boundaries between the organs shown in the image. The higher resolution of the anatomical imaging system is evident in the smaller size of the pixels used in the data acquisition and the reconstruction matrix.

During operation, the PET or SPECT imaging system 14 identifies positrons or gamma rays, respectively, which are emitted by radio nuclides previously injected into a patient and within a target, which may be an organ or lesion of interest. Hereinafter, in the interest of simplifying this explanation, an organ or lesion to be examined will be referred to as the target and will be included in an "area of interest" that is larger than the target. The area of interest may be included in a larger viewing area that includes some surrounding tissue containing background radiation. In PET studies, after the radiopharmaceutical becomes concentrated within the area of interest and while the radionuclides decay, the radionuclides emit positrons. The positrons travel a very short distance before they encounter an electron and, when the positron encounters an electron, the positron is annihilated and convened into two photons, or gamma rays. The annihilation events are recorded by the PET imaging system 14 as an emission data set 18. The emission data set 18 is then used to reconstruct a physiological image 20 including the target within the larger area of interest. Similarly, in SPECT studies, single photon emitting isotope or isotopes are used. The emission data set 18 is processed to reconstruct a three-dimensional (3D) physiological image 20 that corresponds to a plurality of two-dimensional (2D) slices taken through the same organ of interest. As compared to the anatomical image 17 generated by the first imaging modality, the physiological image 20 is a low resolution image that includes "fuzzy" borders between organs and areas of interest, such as lesions.

As shown in FIG. 1, the combined imaging system 10 includes a workstation 98 that executes an image enhancement module 25 that includes both a mask construction module 22 and an image registration module 23. The mask construction module 22 generates a target boundary from the anatomical image 17 created by the CT or MRI imaging system 12. The target boundary created by the mask construction module 22 is applied to the image 20 generated by the NM imaging system 14 in a registration module 23 to create a combined image 24. The combined image 24 generated by the image enhancement module 25 include a much more accurate volumetric definition of the area of interest, which allows for a more accurate extraction of numerical parameters based on the more accurate definition. Specifically, the combined image enhances the resolution and definition of the organ for lesion of interest relative to the physiological image 20 created by the PET imaging system while allowing the combined image to maintain the radiation image information.

The combined imaging system 10 shown in FIG. 1 further includes a module 100 that better defines the values within and optionally outside of the target boundary utilizing the techniques described below. These adjusted numerical parameters allow for a more accurate calculation of relevant medical parameters from the physiological image 20, which can include the average pharmaceutical concentration in the target and the total pharmaceutical in the target. The corrected physiological image 102 can be displayed for review.

Figure 2A:
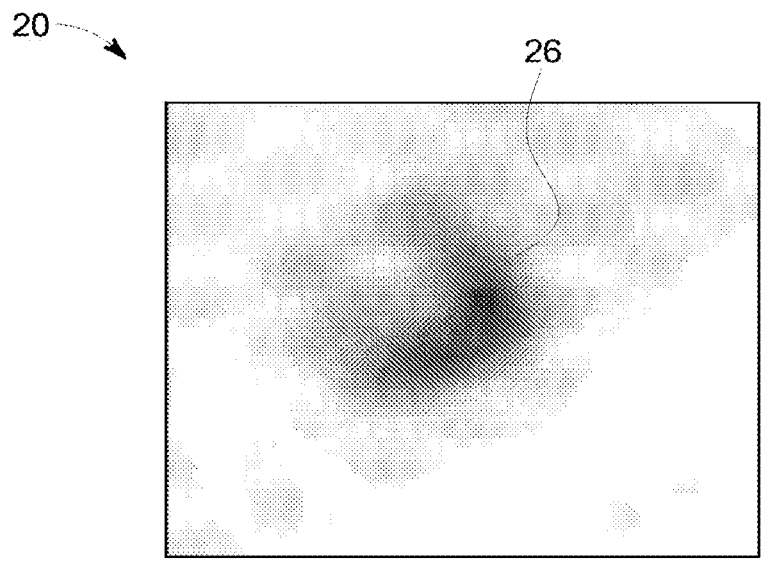
FIG. 2A is a physiological image from a nuclear (NM) imaging system.

FIG. 2A illustrates a portion of a physiological image 20 taken utilizing the NM imaging system 14 shown in FIG. 1. The physiological image 20, as with the images presented in the remaining Figures, are 2D slices of a 3D image. The physiological image 20 includes a target 26, shown by the dark area of FIG. 2A, within the larger area of interest defined by the image parameters. Because of the low resolution and low quality of the physiological image from the NM imaging system, the physiological image 20 is often "low pass" filtered so as not to show the random noise and pixelated nature of the image. However, the calculations and corrections methods disclosed herein may be applied to the un-filtered image. It should be noted that often the radiopharmaceutical concentration in the target is often higher than in the non-target areas, a situation named "hot target". However, the disclosed methods may be applied to "cold targets" therein the radiopharmaceutical concentration in the target is lower than in the non-target areas. As can be seen in FIG. 2A, the target 26 can be identified but the boundaries of the target 26 cannot be easily defined.

Figure 2B:
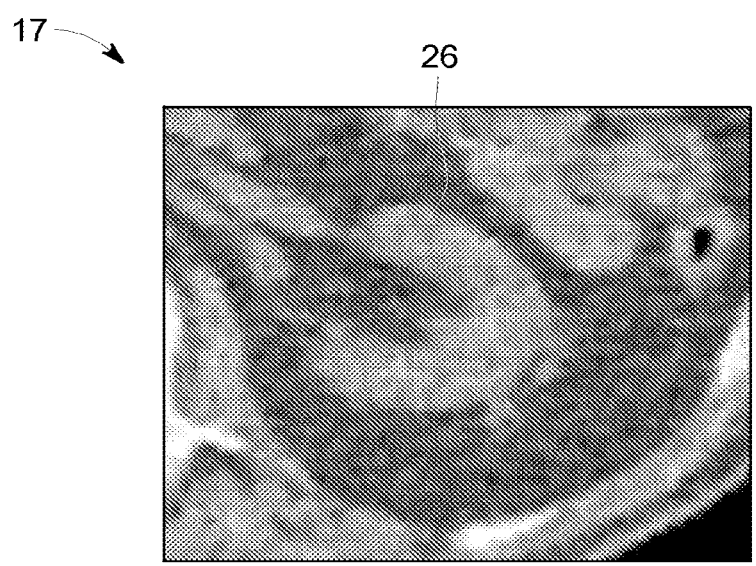
FIG. 2B is an anatomical image from a CT imaging system.

FIG. 2B shows an anatomical image 17 of the same section of the patient as shown in FIG. 2A. The anatomical image 17 is taken from a CT imaging system 12 and includes the same target 26. As can be seen by the comparison between the physiological image 20 shown in FIG. 2A and the anatomical image 17 shown in FIG. 2B, the target 26 is much more defined and includes boundaries between the target and other organs of the patient. As with the image of FIG. 2A, the anatomical image 17 shown in FIG. 2b is a 2D slice of a 3D image. As such, the target 26 is a 3D structure that has a volume.

Figure 2C:
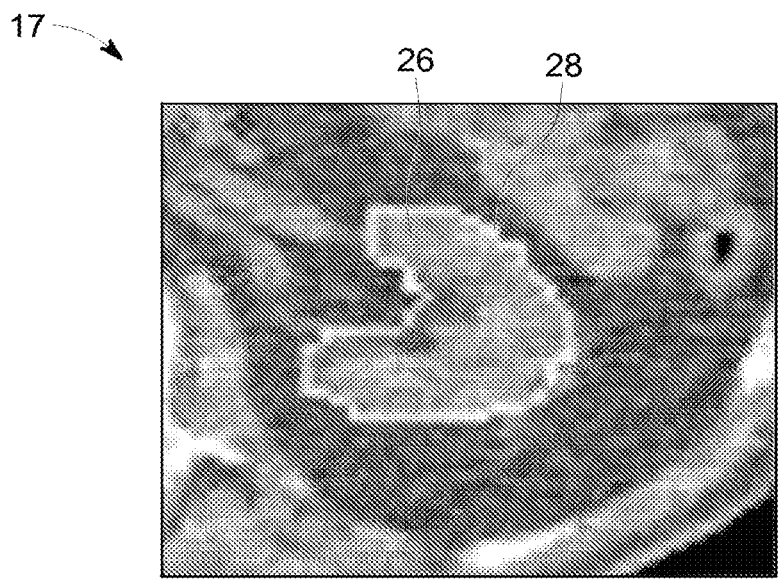
FIG. 2C is an anatomical image similar to FIG. 2B with a target boundary shown for the target area.

Referring now to FIG. 2C, the anatomical image 17 is shown with a calculated target boundary 28 that surrounds the target 26. The target boundary 28 is determined utilizing well known image processing modules that define and mark the target boundary on the anatomical image 17. The target boundary 28 surrounds and defines the target 26 within the larger area of interest defined by the outer parameters of the anatomical image 17.

Figure 2D:
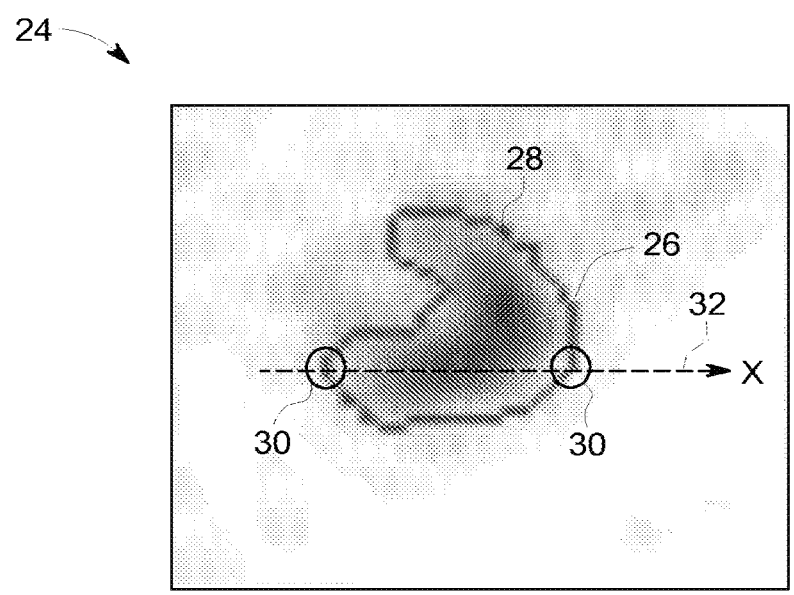
FIG. 2D is combination image showing the target boundary from the anatomical image registered onto the physiological image.

FIG. 2D illustrates a combined image 24 in which the target boundary 28 determined from the anatomical image 17 in FIG. 2C is overlaid on the physiological image 20 of FIG. 2A. The workstation can utilize various different algorithms to align and register the images from the CT and PET imaging systems. As an illustrative example, U.S. Pat. No. 8,391,578, the disclosure of which is incorporated herein by reference, discusses a method and apparatus for automatically registering images from both a CT imaging system 12 and a PET imaging system 14. A similar method and apparatus can be utilized while operating within the scope of the present disclosure. The target 26 shown in the combined image 24 is thus defined by the target boundary 28 determined from the anatomical image 17. The volume of the target, referred to as V-target, can be accurately calculated from the target boundary 28. However, in the transition areas 30 near the target boundary 28, the low resolution of the physiological image causes uncertainties in the accuracy in accounting for radioactivity that is in the target and the activity that is in the non-target areas. In the image shown in FIG. 2D, two examples of the transition areas 30 are shown along a reference axis 32. The inaccuracies in the combined image 24 in the transition areas 30 are caused by two separate effects, referred to as the partial volume effect and the low spatial resolution effect. The partial volume effect is caused by the large size of the voxels used in the physiological image 20 while the low spatial resolution effect is caused by the low resolution of the NM imaging system and the low pass filtering during or post reconstruction.

Figure 3A:
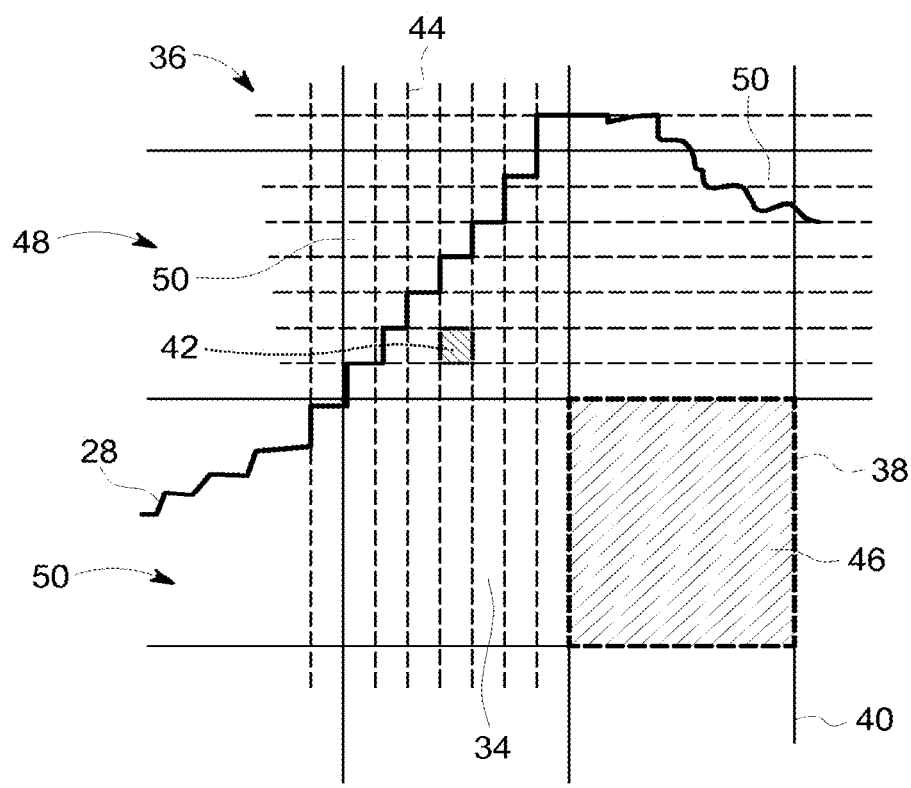
FIG. 3A is a schematic illustration showing the voxels from both the CT and NM imaging systems.

FIG. 3A schematically illustrates the inaccuracies that are created by the partial volume effect of the physiological image. In the illustration of FIG. 3, the target boundary 28 of the target, as determined from the anatomical image, is shown. The target is located on the interior 34 of the target boundary 28 while the background 36 of the physiological image is shown to the exterior 36 of the target boundary 28. In FIG. 3A, the individual voxels 38 of the physiological image are shown by reference numeral 38 and are defined by the grid lines 40. The individual voxels from the anatomical image are shown by reference numeral 42 and are defined by the grid lines 44. As can be clearly seen in FIG. 3A, the size of the voxel 38 within the physiological image is much larger than the size of the voxel 42 from the anatomical image. The target boundary 28 is defined by the individual voxels 42 from the anatomical image as illustrated.

As can be understood in FIG. 3A, the voxels 38 from the physiological image include multiple inner voxels 46 that are contained completely within the target boundary 28 and a series of outer voxels 48 that are contained completely outside of the target boundary 28. However, there are multiple voxels that are partially inside and partially outside of the target boundary 28. These voxels, shown by reference numeral 50, are referred to as partial volume voxels 50.

The inaccuracy created in the anatomical image by the partial volume effect can be clearly seen in FIG. 3A.

Figure 3B:
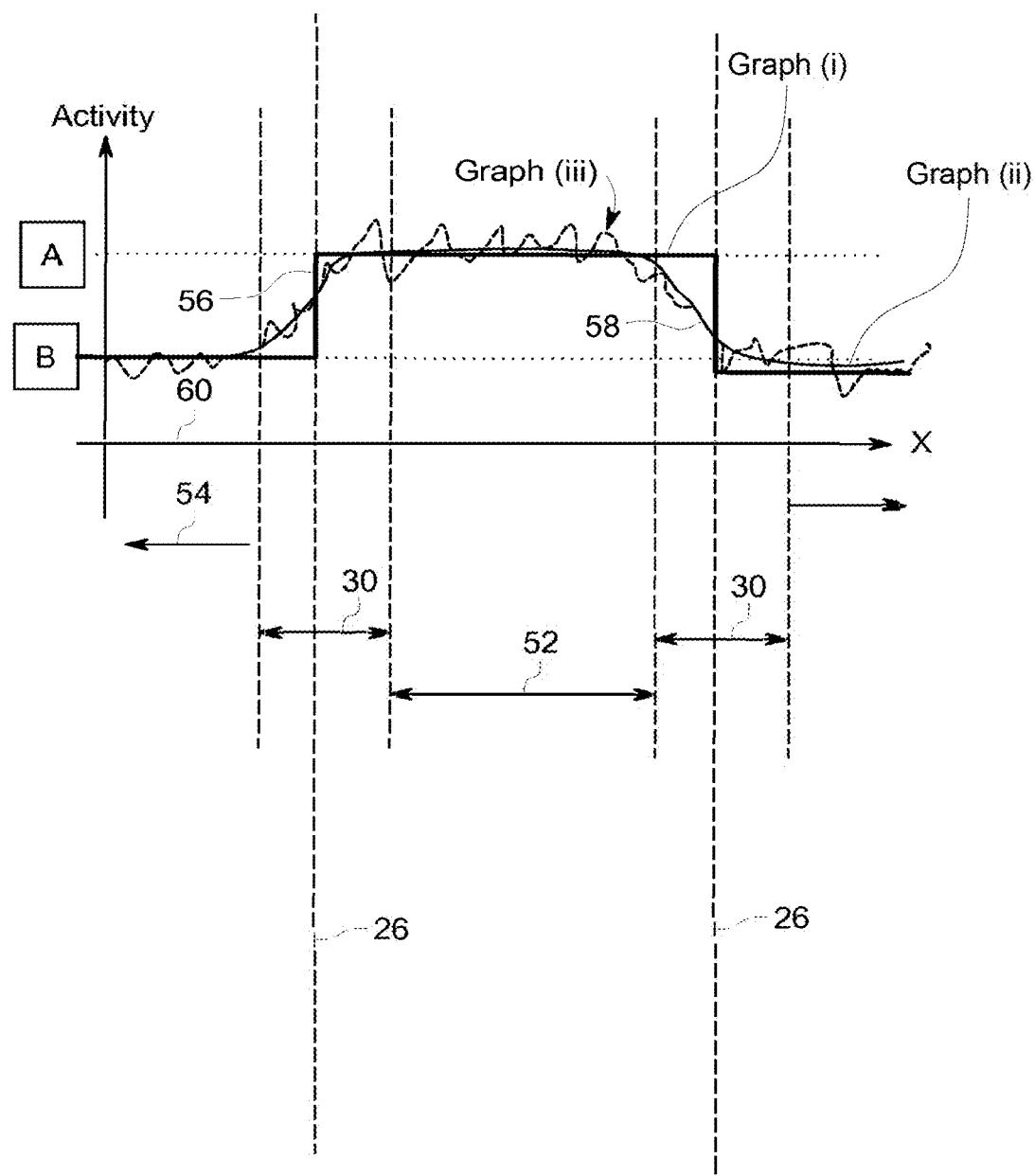
FIG. 3B is a schematic illustration of the activity levels within and outside of the target boundary.

FIG. 3B illustrates a schematic graph of the radiopharmaceutical concentration in the target, non-target and transition regions along the reference axis 32 shown in FIG. 2D. The transition areas 30, which are shown in FIG. 2D, are represented in the schematic graph of FIG. 3B. The area of the target clearly within the boundary is shown by reference area 52 while the area clearly outside of the boundary is shown by the reference areas 54. The target boundary 26 is shown by the lines in FIG. 3B.

The resolution of the NM imaging system 14 is limited mainly by the collimator used in the system and to a lesser degree by the intrinsic resolution of the NM detector. In contrast to the fixed intrinsic resolution of the NM detector, the collimator broadening increases rapidly with the distance from the target to the collimator and thus is not constant throughout the image. Although some reconstruction algorithms include "resolution recovery" modules, some broadening of the features is unavoidable. The noisy data acquired in the NM imaging system may requires some post filtering of the image, which also contributes to the broadening effect.

In FIG. 3B, graph (i) represents the true value as assumed to be in the imaged subject. In this ideal graph, the values within the target area 52 have a value of A (for activity) while the value for the non-target area 54 is represented by value B (for background). In the representation of graph (i), the transition from the non-target zone 54 to the target zone 52 is represented by the vertical line 56.

Graph (ii) represents the values that should be seen in the physiological image in the absence of any noise. Once again, the values in the clearly non-target zone 54 are represented by level B while the values in the clearly target zone 52 are represented by the value A. In the transition zone 30, the graph in area 58 makes a smooth transition from the activity level A to the activity level B and back.

Graph (iii) represents the actual values as measured by a typical anatomical image. Graph (iii) is widely varying in values although the general shape of the graph follows the contours of graph (ii). As illustrated in FIG. 3B, both the background radiation level B and the target radiation level A are above a baseline value 60 since both the background and the target receive some of the radiation.

Figure 4:
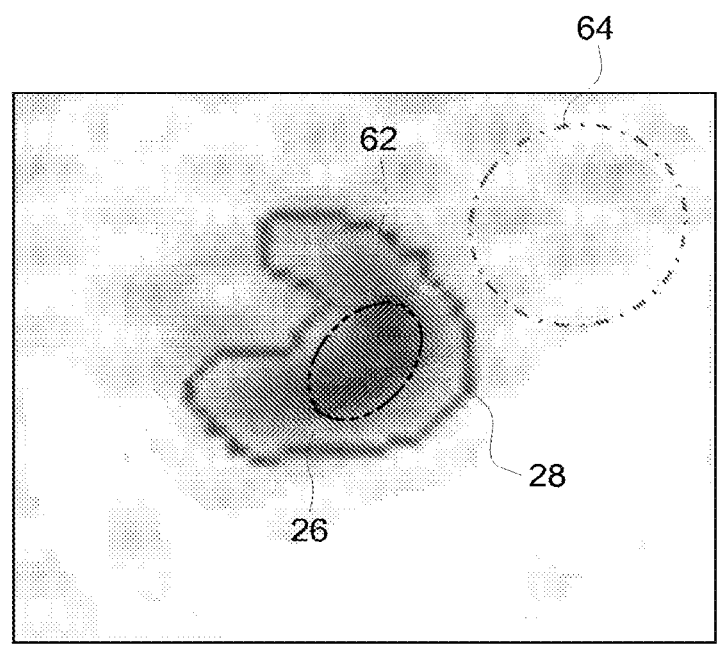
FIG. 4 is a physiological image showing both an inner and outer region of interest in accordance with a prior art method.

FIG. 4 illustrates a representation of a prior art, conventional method used to determine parameters from the physiological image, such as the average and total uptake in the target 26. As illustrated in FIG. 4, an inner region of interest (Inner ROI) 62 is typically marked clearly within the target 26 by a user. The Inner ROI 62 is typically marked within the target 26 in an area that avoids the transition zone near the calculated target boundary 28. Both the volume (V-inner) and the activity (A-inner) may be calculated from the Inner ROI without being affected by the area of the target near the transition zone.

The Estimated Average Target activity (EAT) can be calculated by EAT=(A-inner)/(V-inner). In principle, the EAT should be equal to the true value A, which is the average activity in the target. However, the calculated EAT takes into account only a fraction of the counts in the target volume and thus is subject to more statistical noise than the data can provide. The fraction of statistical noise increases as the target size is smaller.

In addition, the Estimated Average Background activity value (EAB) can be calculated from the non-target region of interest 64 (FIG. 4) that is clearly located away from the target and the target boundary 28. Generally, the size of the non-target ROI 64 may be defined large enough such that the EAB value is less susceptible to noise and is close to the value B shown in FIG. 3B.

Once the EAT and EAB are calculated from FIG. 4, the Target to Background Ratio (TBR) can be calculated as TBR=EAT/EAB. The EAT and TBR may be used to diagnose medical conditions, such as the malignancy of lesions, etc. Typically, these calculations are performed on the physiological image from the NM imaging system without the use of the anatomical image from the CT imaging system since the transition zones may be judged from only the physiological image.

In addition to these calculations, the Total Activity in the Lesion (TLA) may be calculated by multiplying the estimated average target activity (EAT) by the lesion volume (LV) determined from the target boundary 28 calculated from the anatomical image from the CT imaging system. The TLA is calculated by TLA=LV×EAT.

Although these types of calculations are typically obtained from the physiological image from the NM imaging system, the accuracy of the calculations can be improved utilizing the methods presented by the present disclosure. The methods described below improve on the estimation of the true radiopharmaceutical distribution within the target, based upon a combination of the anatomical and physiological image data.

The first method of improving the estimation of the radiopharmaceutical distribution within the target corrects for the partial volume effect described previously. Referring back to FIG. 3A, the first step in this method defines a "binary mask" on the voxel space in the physiological image. The voxels 38 of the physiological image are shown by the grid lines 40 in FIG. 3A. In the first step of this method, the matrix assigns the value "1" to all of the voxels 38 that are located completely within the target boundary 28. These inner voxels 46 are clearly within the target boundary 28. The method then assigns the value of "0" to all other voxels, including both the outer voxels 48 located completely to the exterior of the target boundary 28 and the partial volume voxels 50 that include the target boundary 28. Thus, each voxel "i" in the physiological image is associated with a matrix value M(i)={0,1} ("i" is the voxels' index that in 3D space is given by the x, y, z indexes of each voxel). Thus, by summing over all "i", the Inner Volume (IV) can be calculated by the equation:

$$\text{Inner Volume} = IV = \Sigma_i M(i) * A(i) \quad \text{(Equation 1)}$$

In Equation 1, V is the volume of one voxel and the summing is done over the entire range of voxels "i". In addition, the Inner Activity (IA) can be calculated utilizing the equation:

$$\text{Inner Activity} = IA = \Sigma_i M(i) * A(i) \quad \text{(Equation 2)}$$

In Equation 2, A(i) is the activity in voxel "i".

Once the inner volume (IV) and the inner activity (IA) have been calculated, the Estimated Target Activity (EAT) can be calculated from EAT=IA/IV.

However, in order to calculate the Total Activity in the Lesion (TLA), correction needs to be carried out to compensate for the fact that activity in the partial volume voxels 50 of the physiological image 20 that include the target boundary 28 is a mixture of target activity A and background activity B.

As illustrated in FIG. 3A, each of the partial volume voxels is shown by reference numeral 50. In accordance with the method of the present disclosure, each of the partial volume voxels "j" is assigned a weight W(j) that is given by the relationship W(j)=I(j)/V. In this equation, I(j) is the volume of voxel "j" that is within the target and V (as already defined) is the volume of the voxel. As illustrated in FIG. 3B, the partial volume voxels 50 located along the target boundary 28 include different volumes of the voxel that are within the target boundary 28 and that are outside of the target boundary 28. The weight W(j) assigned to each of the partial volume voxels allows for the inclusion of the partial volume voxels in the Lesion Volume (LV). The accurate lesion volume (LV) can be added to the inner volume IV as shown by the equation below:

$$\text{Lesion Volume}=LV=IV+\Sigma_j W(j)*V \qquad \text{(Equation 3)}$$

Wherein "j" are the partial volume voxels and W(j) are the weights corresponding to the part of voxel j within the target. In accordance with the present disclosure, there are a few different ways contemplated of calculating the activity in the partial volume voxels "j" (PVA) in order to add it to the inner activity (IA) in order to get the estimated total lesion activity (TLA) where TLA=IA+PVA.

In the first of these possible methods, the target activity in each of the partial volume voxels "j" is replaced with the average target activity (EAT). In such analysis, the partial volume activity (PVA) can be calculated utilizing the following equation:

$$\text{Partial Volume Activity}=PVA=\Sigma_j W(j)*EAT \qquad \text{(Equation 4)}$$

In this calculation, the weight W(j) of each partial volume voxel is multiplied by the average target activity EAT and the partial volume activity is summed overall and only the partial volume voxels "j". Once calculated, the PVA is added to the Inner Activity IA to determine the Total Lesion Activity TLA. Thus the corrected target activity is then given by TLA=PVA+IA.

In another alternate method, for each partial volume voxel 38, the target activity in the partial volume voxel "j" is extracted by assuming that the non-target activity in the voxel is given by the equation (1−W(j))*EAB. Therefore, the non-target section in the partial volume voxel is filled with the average background activity. In such a method, the target activity in each partial volume voxel "j", TA(j) is given by the equation TA(j)=A(j)−(1−W(j))*EAB, where A(j) is measured by the activity in the voxel "j". In such a case, the partial volume activity (PVA) is given by the equation:

$$PVA=\Sigma_j TA(j) \qquad \text{(Equation 5)}$$

In this case, the total lesion activity can be calculated as TLA=IA+PVA and the estimated average target activity (EAT) can be calculated from EAT=TLA/LV.

In addition to the methods described above, the present disclosure also contemplates a method for correcting for the low spatial resolution effect.

Figure 5A:
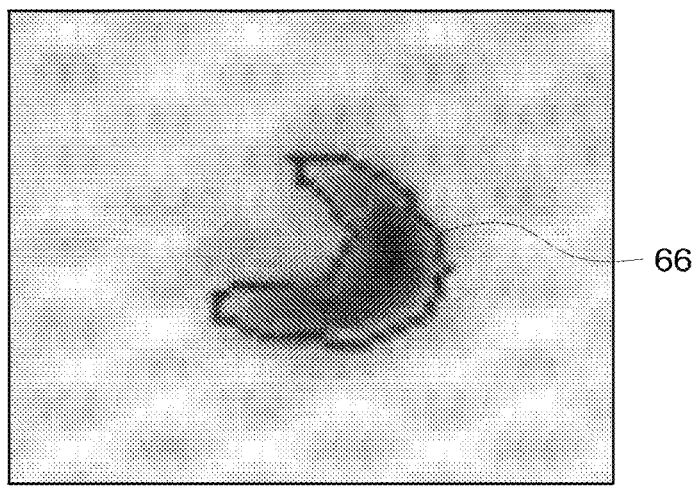
FIG. 5A is a physiological image with an eroded boundary within the target.

Referring now to FIG. 5A, the physiological image 20 similar to FIG. 2A is shown with an eroded boundary 66 that marks a portion of the image as being clearly part of the target, which is shown by region 52 in FIG. 3B. The eroded boundary 66 shown in FIG. 5A is derived by moving the boundary slightly inward from the target boundary 28 estimated from the anatomical image 17 from the CT imaging system 12, as best shown in FIG. 2D. The eroded boundary 66 is derived by moving inward from the target boundary 28 by a known distance. The known distance may be fixed or determined from the camera parameters and the reconstruction parameters or is measured by imaging a source phantom with sharp boundaries on the same camera in similar conditions. The resolution of NM systems, and specifically SPECT systems, may vary from one system to the other. Even with the same system, and using the same collimator, the resolution may depend on the location within the image and specifically the depth of the location within the image. The effective width of the transition zone may be estimated from the image itself and be used in the correction algorithm. The effective width may be different on different locations on the same border surface or on different targets in the same image.

The activity measured in the voxels within the eroded boundary 66 is not influenced by image smearing, background radiation, or the partial volume effects. From this eroded boundary 66, the Inner Activity (IA) and the Inner Volume (IV) are calculated as described above. In such a calculation, an assumption is made that the inner volume has a uniform activity within the eroded boundary. The activity within the inner volume is more uniform as a whole than the overall image, which could include several organs. Once these two values are calculated, the Estimated Average Target activity (EAT) can be calculated by EAT=IA/IV.

Figure 5B:
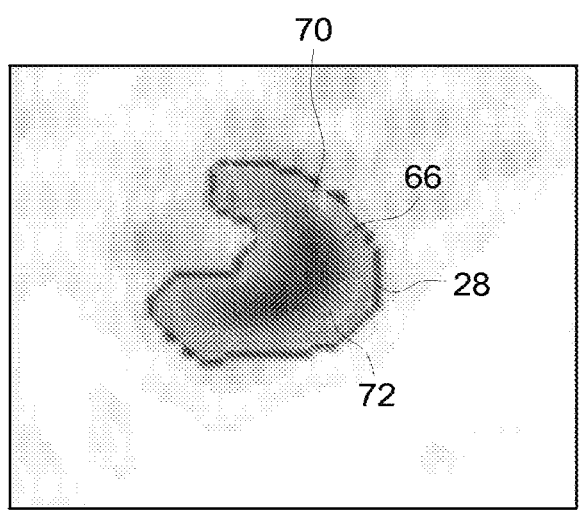
FIG. 5B is a corrected physiological image.

Once this EAT has been calculated, the method replaces the voxels that are within the target boundary 28 shown in FIG. 2D but outside the eroded boundary 66 shown in FIG. 5A. The voxels that are within the target boundary 28 and outside of the eroded boundary 66 are replaced with the value of the calculated EAT. FIG. 5B shows the corrected physiological image 68 after replacing the values of the voxels that are within the target boundary 28 but outside the eroded boundary 66 with the values of the calculated EAT. This correction band 70 shows up as a uniform band that is just inward of the target boundary 28. Although this image may be unpleasant to the eye as it appears unnaturally noise-free and uniform, the correction according to the method of the disclosure improves the calculations made from the physiological image 20. In some embodiments, statistical noise can be added to the values of the voxels in this correction band 70 to make it blend with the noisy image in the area 72 interior from the eroded boundary 66. Since positive and negative values representing the noise are added to the voxel values in the correction band 70, the total activity within the correction band 70 changes very little, if at all.

In the embodiment illustrated, the target may be a full organ of interest, not just a lesion. For example, the average concentration or total activity in the target may be used to estimate energy imposed during radionuclide therapy to determine treatment effectiveness. Similarly, for example, average concentration or total activity in the target may be used to estimate energy imposed during radionuclide imaging to determine (and avoid) over-exposure and damage to the patient.

Since the activity in the image 68 outside of the target boundary 28 is of little medical significance, the activity value of voxels within the transition zone 70 but outside of the target boundary 28 are usually left uncorrected. It is, however, possible to replace these values with the average background value EAB. This will affect the display corrected image, but not the calculated parameters.

Figure 6:
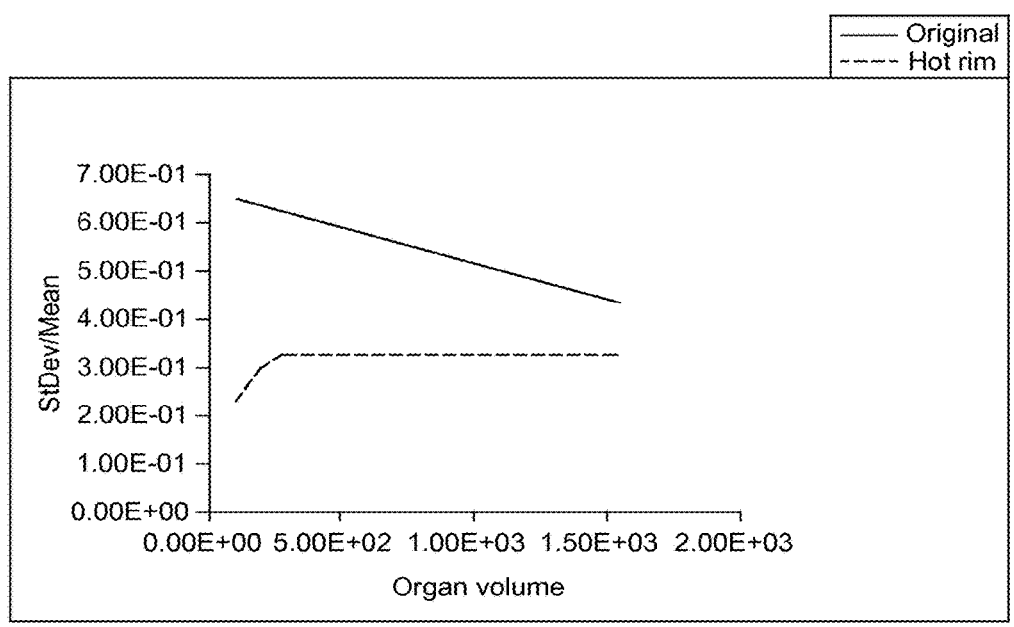
FIG. 6 is a graph showing the improvement in the volume calculation.

FIG. 6 illustrated the change in the standard deviation to mean in the original calculated volume of an organ relative to the calculated volume utilizing the system and method of the second embodiment of the present disclosure. Small the standard deviation to mean ratio is indicative of improved accuracy. As can be seen in these graphs, target parameters calculated utilizing prior art methods display large relative deviations for targets with small volumes (large standard deviation divided by the mean value of the calculated lesion average activity). In contrast, the deviation for parameters calculated from the second embodiment of the disclosure ("hot rim") is smaller stable and smaller for all target volumes.

As indicated previously, the resolution of the physiological image from the NM imaging system is degraded due to several different effects, including both the camera's resolution and reconstruction effects. The resolution of the camera is influenced by both the detector's intrinsic resolution, which depends upon the type of detector, and to some extent, the isotope utilized. The camera resolution is also affected by collimator broadening, which depends upon the type of collimator used and degrades rapidly with the distance of the imaged target to the face of the collimator. As such, the resolution degradation is different for each target.

The resolution of the physiological image is also affected by the reconstruction process. Specifically, the physiological image may be reconstructed onto voxels of larger size than utilized in an anatomical image. When a filter back projection (FBP) algorithm is used, the filter is well known and can be applied before or after the back projection.

Figure 7:
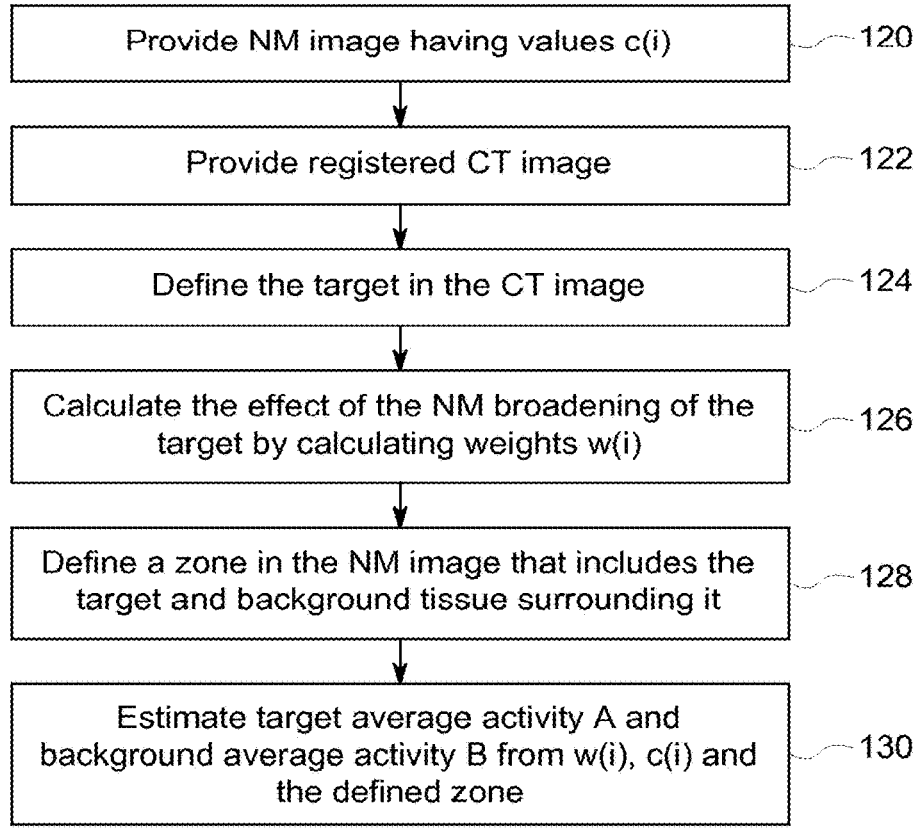
FIG. 7 is a flow chart of one method of the present disclosure.

In accordance with the present disclosure, additional methods are provided for estimating the target average activity (A) and the background average activity (B) using a measured physiological image and a measured anatomical image. Initially, it is assumed that in the physiological image from the NM imaging system, a data set of measured radioactivity "c(i)" are available for each large voxel "i". In accordance with the present disclosure, as illustrated in FIG. 7, the method initially provides a physiological image that includes values for c(i), as shown in step 120. The physiological image is registered with the anatomical image, as illustrated in step 122. The target area is defined in the anatomical image as shown in step 124. Once these steps have been completed, the method of FIG. 7 calculates the effect of NM broadening of the target by calculating a weight W(i) for each voxel "i" within the NM image as shown in step 126. The broadening calculated in step 126 causes the voxels near the target boundary to be influenced by both the activity in the target and the activity in the background. Assuming that the target activity is uniform and has the value A and the background activity is also uniform and has the value B, the broadening is characterized for each voxel of the physiological image by a weight W(i). In the absence of any noise, errors and non-uniformities, the measured activity c(i) should be given by the equation $c(i)=A*W(i)+B*(1-w(i))$.

At this step, W(i) is calculated in a zone that includes the target and some background surrounding the target. The calculation zone must be large enough such that the outer boundary is outside of the broadening of the target caused by the NM imaging system resolution. For example, the background zone may be defined as a box around the target where the edges of the box are outside of the target by more than the broadening length. The background zone should be large enough as to have enough background tissue such that the value B can be found accurately. However, the zone should also be limited in size such that the assumption of constant background activity remains valid. For example the zone may be determined by a process opposing the creation of eroded boundary 66, that is moving the boundary outward. Since the values of c(i) are measured, the method calculates the values of the average activity A and the background average activity B as illustrated in step 130. The step of estimating the values of A and B can be done utilizing well known mathematical models known in the art. As an example, for each voxel "i" in the zone, the difference e(i) between the measured and assumed activity may be given as $e(i)=A*W(i)+B*(1-W(i))-c(i)$.

A good estimation for the values of A and B is one that minimizes the accumulated square error or for the values of A and B that minimizes the error E given by the expression $\Sigma e(i)^2$, where the sum is over all of the voxels "i" in the zone. Finally, the values of A and B can be calculated by demanding that the partial derivative $d/dA[E]=0$ and $d/dB[E]=0$.

Based upon the above, the method must find the weight W(i) set out in step 126 shown in FIG. 7.

In accordance with the present disclosure, two methods are contemplated for determining the weight W(i). The first of these methods calculates the weight W(i) due to the difference in the size of the voxels in both the anatomical image and the physiological image as described previously in the present disclosure. As a further step, to add the effect of the reconstruction, the same filter is used and the reconstruction is applied to the "image" having the values W(i) as a post processing low pass filter. The resulting image W'(i) is now used to estimate the values A, B. It should be noted that in FBP reconstruction, the low pass filter is applied before the back projection to speed the calculation. However, the equivalent filter may be determined and applied as a post processing filter.

Figure 8:
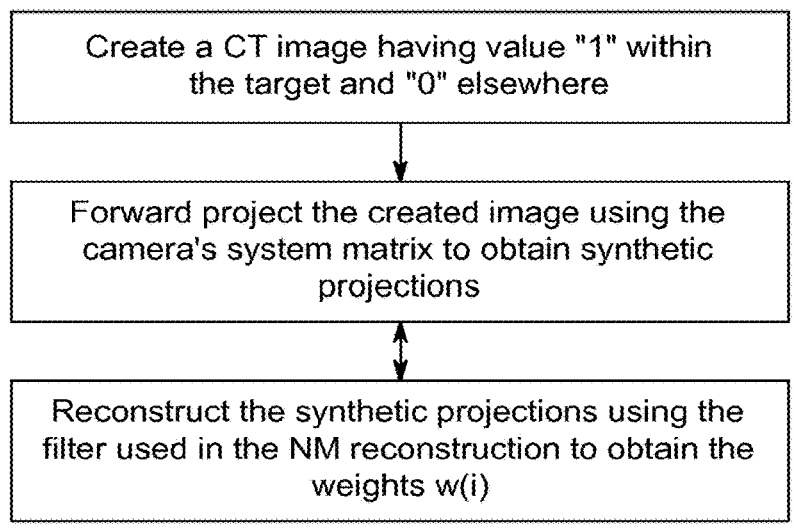
FIG. 8 is a flow chart showing one method of calculating a weight for a voxel in the physiological image.

In a second method, as shown in FIG. 8, the calculated weights w(i) take into account all of the broadening mechanisms, including camera resolution, the course grid used in the physiological image and the filter used in reconstruction. In this method, the CT image is used to create an image in which all of the voxels within the target have a value of 1 and those outside of the target have a value of 0. The created image is forward projected onto a synthetic virtual camera using the camera actual parameters known as "system matrix". Forward projection is well known in the art and creates a set of synthetic projections that exhibit the resolution loss due to the collimator and detector. From the forward projected synthetic projections, an image is reconstructed utilizing the same voxel grid and FBP filter used for the physiological image reconstruction. The resulting image has values W'''(i) that are influenced by both the camera resolution degradation (the result of the forward projection) and the reconstruction and filtering loss of resolution (the result of the FBP). The resulting image including weight W'''(i) are now used to calculate and estimate A and B.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A method comprising:
   reconstructing an anatomical image having a first resolution using a first imaging modality;
   reconstructing a physiological image having a second resolution lower than the first resolution using a second imaging modality, the physiological image including a plurality of voxels;

identifying a target boundary of the target in the anatomical image;
registering the target boundary of the target on the physiological image;
identifying voxels of the physiological image that are completely within the target boundary;
calculating an inner activity value by summing activity levels of the voxels of the physiological image completely within the target boundary;
identifying partial volume voxels of the physiological image that include the target boundary;
assigning a weight to each of the partial volume voxels;
multiplying the weight of each partial volume voxel by an average target activity level to determine a modified activity level for each partial volume voxel;
calculating a partial volume activity value by summing the modified activity levels of the partial volume voxels;
combining the inner activity value and the partial volume activity; and
modifying the physiological image using the combined inner activity value and partial volume activity to provide a corrected physiological image.

2. The method of claim 1 wherein the weight assigned to a given one of the partial volume voxels is based on a volume of the given one of the partial volume voxels within the boundary.

3. The method of claim 1 wherein the first imaging modality is a computed tomography (CT) imaging system.

4. The method of claim 1 wherein the second imaging modality is a nuclear imaging modality.

5. A multi-modality imaging system comprising:
a first imaging modality apparatus operable to reconstruct an anatomical image of a target, the anatomical image having a first resolution;
a second imaging modality apparatus operable to reconstruct a physiological image of the target, the physiological image having a second resolution lower than the first resolution;
an image enhancement module comprising at least one processor programmed to:
acquire the anatomical image from the first imaging modality apparatus;
acquire the physiological image from the second imaging modality apparatus, the physiological image including a plurality of voxels;
identify a target boundary of the target in the anatomical image;
register the target boundary of the target to the physiological image;
identify voxels of the physiological image that are completely within the target boundary;
calculate an inner activity value by summing activity levels of the voxels of the physiological image completely within the target boundary;
identify partial volume voxels of the physiological image that include the target boundary;
assign a weight to each of the partial volume voxels;
multiply the weight of each partial volume voxel by an average target activity level to determine a modified activity level for each partial volume voxel;
calculate a partial volume activity value by summing the modified activity levels of the partial volume voxels;
combine the inner activity value and the partial volume activity; and
modify the physiological image using the combined inner activity value and partial volume activity to provide a corrected physiological image.

6. The multi-modality imaging system of claim 5 wherein the weight assigned to each of the partial volume voxels is based on a volume of the partial volume voxel within the target boundary.

7. A non-transitory computer-readable medium encoded with a program to instruct a computer to:
acquire an anatomical image having a first resolution using a first imaging modality;
acquire a physiological image having a second resolution lower than the first resolution using a second imaging modality, the physiological image including a plurality of voxels;
identify a target boundary of the target in the anatomical image;
apply the target boundary of the target to the physiological image;
identify voxels of the physiological image that are completely within the target boundary;
calculate an inner activity value by summing activity levels of the voxels of the physiological image completely within the target boundary;
identify partial volume voxels of the physiological image that include the target boundary;
assign a weight to each of the partial volume voxels;
multiply the weight of each partial volume voxel by an average target activity level to determine a modified activity level for each partial volume voxel;
calculate a partial volume activity value by summing the modified activity levels of the partial volume voxels;
combine the inner activity value and the partial volume activity; and
modify the physiological image using the combined inner activity value and partial volume activity to provide a corrected physiological image.

* * * * *